(12) United States Patent
Reynolds et al.

(10) Patent No.: US 10,751,178 B2
(45) Date of Patent: Aug. 25, 2020

(54) INTRODUCER WITH EXPANDABLE CAPABILITIES

(71) Applicant: BOSTON SCIENTIFIC SCIMED, INC., Maple Grove, MN (US)

(72) Inventors: Brian R. Reynolds, Ramsey, MN (US); Ross A. Olson, Anoka, MN (US); James M. Anderson, Corcoran, MN (US); Heather Hetteen, Robbinsdale, MN (US); Adam David Grovender, Maple Grove, MN (US); Uchenna Junior Agu, Baton Rouge, LA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 128 days.

(21) Appl. No.: 15/892,524

(22) Filed: Feb. 9, 2018

(65) Prior Publication Data

US 2018/0221149 A1  Aug. 9, 2018

Related U.S. Application Data

(60) Provisional application No. 62/456,818, filed on Feb. 9, 2017.

(51) Int. Cl.
*A61F 2/24* (2006.01)
*A61M 25/00* (2006.01)

(52) U.S. Cl.
CPC ....... *A61F 2/2436* (2013.01); *A61M 25/0023* (2013.01); *A61M 25/0045* (2013.01);
(Continued)

(58) Field of Classification Search
CPC ............ A61F 2/2436; A61F 2210/0014; A61F 2250/0098; A61M 25/0023;
(Continued)

(56) References Cited

U.S. PATENT DOCUMENTS 6,080,141 A     6/2000  Castro et al.
2005/0080430 A1* 4/2005  Wright, Jr. ....... A61B 17/22031
                                                      606/108
(Continued)

FOREIGN PATENT DOCUMENTS

EP          1660167 A2    5/2006

OTHER PUBLICATIONS

International Search Report and Written Opinion dated May 28, 2018 for International Application No. PCT/US2018/017539.

*Primary Examiner* — George J Ulsh
(74) *Attorney, Agent, or Firm* — Seager, Tufte & Wickhem LLP

(57) ABSTRACT

An example introducer is disclosed. An example introducer includes a tubular member including an inner layer and an outer layer, the inner layer having an inner surface, an outer surface and wall extending therebetween. The outer layer is disposed along the outer surface of the inner layer. The inner layer includes a plurality of longitudinal channels extending radially outward from the inner surface. Each channel of the plurality of channels has a circumferential width. Further, the tubular member is designed to shift from an unexpanded configuration to an expanded configuration, wherein the width of each channel increases as the tubular member shifts from the unexpanded configuration to the expanded configuration.

17 Claims, 9 Drawing Sheets

(52) U.S. Cl.
CPC . *A61M 25/0074* (2013.01); *A61F 2210/0014* (2013.01); *A61F 2250/0098* (2013.01); *A61M 25/005* (2013.01); *A61M 2025/0024* (2013.01)

(58) Field of Classification Search
CPC .......... A61M 25/0045; A61M 25/0074; A61M 2025/0024; A61M 25/005
See application file for complete search history.

(56) References Cited

U.S. PATENT DOCUMENTS

2010/0094392 A1    4/2010   Nyguen et al.
2013/0178711 A1    7/2013   Avneri et al.
2016/0296332 A1   10/2016   Zhou et al.

* cited by examiner

INTRODUCER WITH EXPANDABLE CAPABILITIES

CROSS-REFERENCED TO RELATED APPLICATIONS

This application claims the benefit of priority under 35 U.S.C. § 119 to U.S. Provisional Application Ser. No. 62/456,818, filed Feb. 9, 2017, the entirety of which is incorporated herein by reference.

TECHNICAL FIELD

The disclosure relates generally to medical devices and more particularly to medical devices that are adapted for use in percutaneous medical procedures.

BACKGROUND

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilize to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough).

SUMMARY

This disclosure provides design, material, manufacturing method, and use alternatives for medical devices. An example introducer includes a tubular member including an inner layer and an outer layer, the inner layer having an inner surface, an outer surface and wall extending therebetween. The outer layer is disposed along the outer surface of the inner layer. The inner layer includes a plurality of longitudinal channels extending radially outward from the inner surface. Each channel of the plurality of channels has a circumferential width. Further, the tubular member is designed to shift from an unexpanded configuration to an expanded configuration, wherein the width of each channel increases as the tubular member shifts from the unexpanded configuration to the expanded configuration.

Alternatively or additionally to any of the examples above, wherein the outer layer extends continuously around the circumference of the inner layer in both the unexpanded configuration and the expanded configuration.

Alternatively or additionally to any of the examples above, wherein each channel of the plurality of channels extends from the inner surface through the wall of the inner layer.

Alternatively or additionally to any of the examples above, wherein the tubular member includes a first outer diameter in the unexpanded configuration and a second outer diameter in the expanded configuration, and wherein the second diameter is at least 125% of the first diameter.

Alternatively or additionally to any of the examples above, wherein the outer layer is free of the plurality of channels.

Alternatively or additionally to any of the examples above, wherein the plurality of channels includes 7-11 channels.

Alternatively or additionally to any of the examples above, wherein the introducer sheath includes a hub member attached to the tubular member, the tubular member including a proximal section and a distal section, and wherein the plurality of channels are distal of the proximal section.

Alternatively or additionally to any of the examples above, wherein the tubular member further comprises a reinforcement layer disposed between the inner layer and the outer layer.

Alternatively or additionally to any of the examples above, wherein the plurality of channels extend radially outward into at least a portion of the reinforcement layer.

Another introducer sheath includes:
a shaft having an expandable portion and a tip member, the expandable portion positioned proximal to the tip member; and
an outer jacket disposed along an outer surface of the shaft;
wherein the expandable portion includes a plurality of longitudinal channels extending radially outward from an inner surface of the expandable portion;
wherein each channel of the plurality of channels has a circumferential width;
wherein both the expandable portion and the tip member are designed to shift from a unexpanded configuration to an expanded configuration, and wherein the width of each channel increases as the expandable portion shifts from the unexpanded configuration to the expanded configuration.

Alternatively or additionally to any of the examples above, wherein the tip member is free of the longitudinal channels.

Alternatively or additionally to any of the examples above, wherein the shaft includes a first outer diameter in the unexpanded configuration and a second outer diameter in the expanded configuration, and wherein the second diameter is at least 125% of the first diameter.

Alternatively or additionally to any of the examples above, wherein the expandable portion includes an outer diameter in the unexpanded configuration, and wherein the tip member includes an outer diameter in the unexpanded state, and wherein the outer diameter of the expandable portion in the unexpanded state matches the outer diameter of the tip member in the unexpanded state.

Alternatively or additionally to any of the examples above, wherein the jacket is free of the plurality of channels.

Alternatively or additionally to any of the examples above, wherein the expandable portion further comprises an inner layer and a reinforcement layer, and wherein the reinforcement layer is disposed between the inner layer and the jacket.

Alternatively or additionally to any of the examples above, wherein the plurality of channels extend radially outward into at least a portion of the reinforcement layer.

Alternatively or additionally to any of the examples above, wherein the plurality of channels extend radially outward through both the inner layer and the reinforcement layer.

A method of treating the heart includes:
positioning an introducer assembly within a body lumen, the introducer assembly including:
a hub;

a shaft having an expandable portion and a tip member, the expandable portion positioned proximal to the tip member; and an outer jacket disposed along an outer surface of the shaft;

wherein the expandable portion includes a plurality of longitudinal channels extending radially outward from an inner surface of the expandable portion;

wherein each channel of the plurality of channels has a circumferential width;

wherein both the expandable portion and the tip member are designed to shift from a unexpanded configuration to an expanded configuration, and wherein the width of each channel increases as the expandable portion shifts from the unexpanded configuration to the expanded configuration; and advancing a heart valve through the introducer assembly, whereby the expandable member expands from an unexpanded configuration to an expanded configuration to accommodate the heart valve.

Alternatively or additionally to any of the examples above, wherein the expandable portion includes an inner layer and a reinforcement layer, and wherein the reinforcement layer is disposed between the inner layer and the jacket.

Alternatively or additionally to any of the examples above, the plurality of channels extend radially outward through both the inner layer and the reinforcement layer.

The above summary of some examples is not intended to describe each disclosed embodiment or every implementation of the present disclosure. The Figures, and Detailed Description, which follow, more particularly exemplify these examples.

Figure 1:
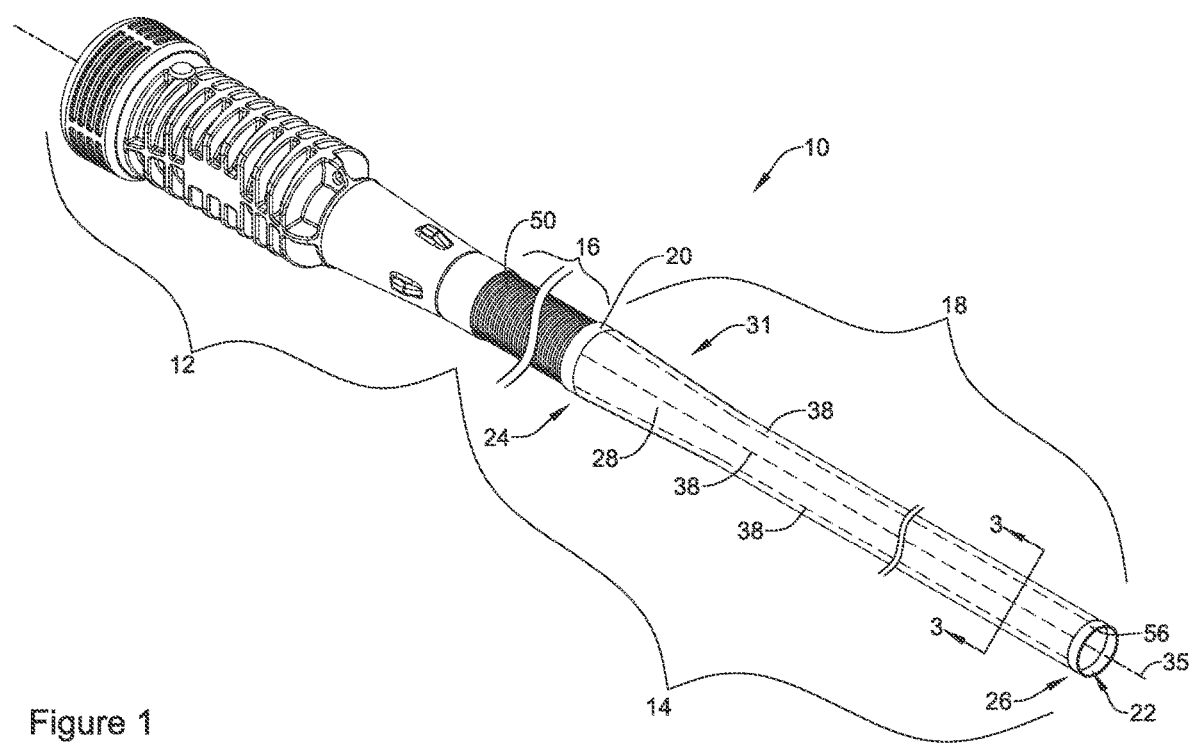
FIG. 1 is a perspective view of an example introducer.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some examples", "other examples", etc., indicate that the embodiment described may include one or more particular features, structures, and/or characteristics. However, such recitations do not necessarily mean that all examples include the particular features, structures, and/or characteristics. Additionally, when particular features, structures, and/or characteristics are described in connection with one embodiment, it should be understood that such features, structures, and/or characteristics may also be used connection with other examples whether or not explicitly described unless clearly stated to the contrary.

The following detailed description should be read with reference to the drawings in which similar elements in different drawings are numbered the same. The drawings, which are not necessarily to scale, depict illustrative examples and are not intended to limit the scope of the disclosure.

FIG. 1 illustrates an example expandable introducer (e.g., delivery sheath, access sheath, etc.) 10. The introducer 10 may include a tubular member 14 attached to a hub member 12. The tubular member 14 may include a proximal section 16 and a distal section 18. The tubular member 14 may further include a lumen 22 extending therethrough. As will be described in greater detail below, an outer jacket or sheath 28 (e.g., an outer layer) may extend along the proximal section 16 and/or the distal section 18.

The introducer 10 may include a tapered region 31. In some examples, the tapered region 31 may be positioned distal to the proximal section 16 of the introducer 10. In some examples at least a portion of the distal section 18 of the introducer 10 may have a substantially constant outer diameter which transitions into the tapered region 31. At least a portion of the tapered portion 31 may have an outer diameter which is greater than the outer diameter of at least a portion of the distal section 18. However, this is not intended to be limiting. It is contemplated that any portion of the introducer 10 may include any number of tapers, constant diameter regions or combinations thereof.

In some examples, the proximal section 16 of the tubular member 14 may include a spring member 50. For example, in some instances, the spring member 50 may be positioned (e.g., laminated) between the outer jacket 28 and an inner layer (not shown in FIG. 1) positioned along the inner surface of the spring member 50.

The hub 12 may include a hemostatic valve or seal disposed therein. The hemostatic valve or seal may prevent blood or other bodily fluid(s) from flowing proximally through the lumen 22 of the tubular member 14 (including the proximal section 16 and the distal section 18). In at least some examples, the hub 12 may include a port in fluid communication with the lumen 22 of the tubular member 14.

As will be described in greater detail below, FIG. 1 further illustrates that the introducer 10 may include one or more channels 38 (depicted by the dashed lines in FIG. 1) extending longitudinally along the inner surface of the distal section 18. The term "channel" used herein is not intended to be limiting. In particular, the longitudinally extending "channels" 38 may also be described as slits, grooves, preferential tear lines, perforations, etc. Further, the channels 38 may extend from a distal end 26 to a proximal end 24 of the distal section 18. Additionally, FIG. 1 illustrates that the proximal end of the channels 38 may terminate at a collar 20. It can further be appreciated from FIG. 1 that the collar 20 may be attached to the proximal section 16 of the tubular member 14 (e.g., the collar 20 may be attached and positioned between the distal end of proximal section 16 and the proximal end of distal section 18). Further, in some examples the collar 20 may be directly coupled to the spring member 50.

In some examples it may be desirable to add a tip member to the distal end of any of the example introducers 10 disclosed herein. FIG. 1 shows an example tip member 56 disposed along the distal end 26 of the distal section 18. The tip member 56 may be designed with a low durometer material. In some instances, a lower durometer material may provide the tip member 56 with the ability to expand (e.g., flex) radially outward and contract radially inward as a variety of medical devices are advanced through the tip member 56. Further, the tip member 56 may include a taper. For example, the tip member 56 may taper from a first diameter to a second diameter at the distal end of the introducer 10. While not intended to be limiting, in some examples the shape of the tip member 56 may resemble a bull-nose. Additionally, the tip member 56 may include a radiopaque material. The radiopaque material may allow the tip member 56 to be visualized by a clinician during a medical procedure. In any of the examples contemplated herein, the tip member 56 may be free of the channels 38.

Figure 2:
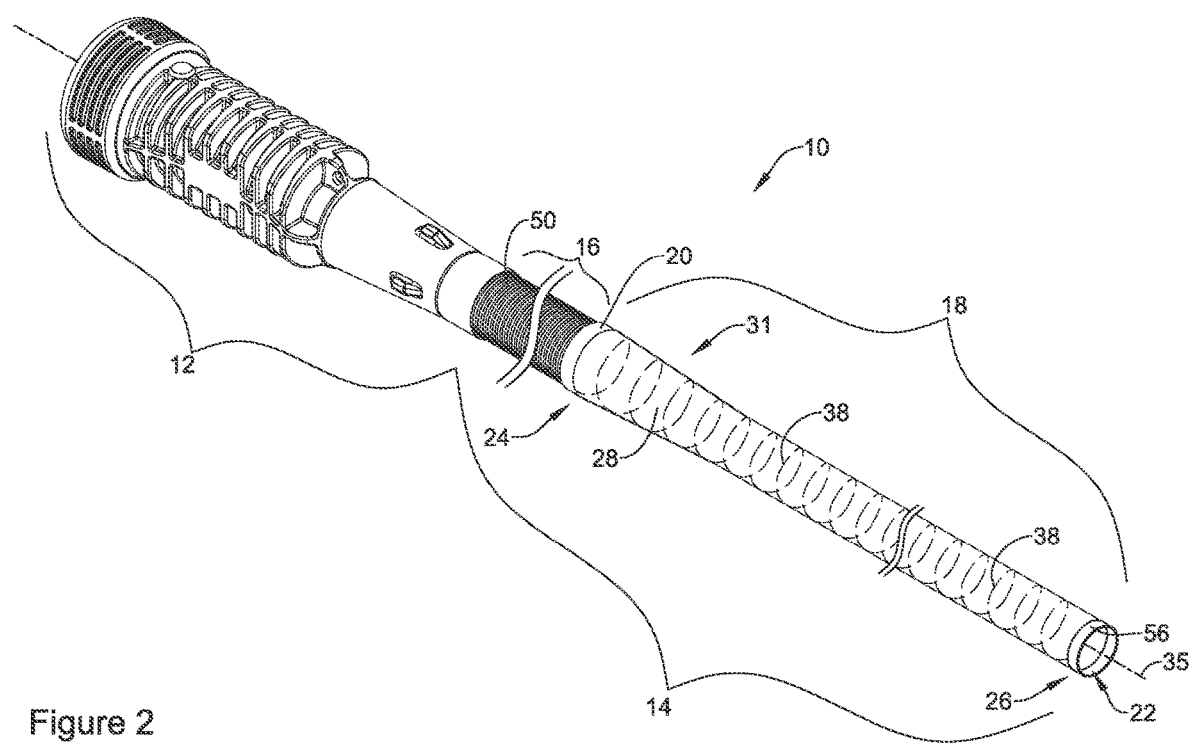
FIG. 2 is a perspective view of another example introducer.

As discussed above, FIG. 1 shows the channels 38 extending longitudinally along the inner surface of the distal section 18. However, other channel configurations are contemplated. For example, FIG. 2 shows an example in which a channel 38 extends along the inner surface of the distal section 18 in a spiral configuration. Similar to the channels 38 described in FIG. 1, the spiral cut channel 38 shown in FIG. 2 may extend from a distal end 26 to a proximal end 24 of the distal section 18. Additionally, FIG. 2 illustrates that the proximal end of the spiral-cut channel 38 may terminate at a collar 20. Further, while FIG. 2 shows a single spiral-cut channel, it is contemplated that multiple spiral channels may extend along the inner surface of the distal section 18.

Figure 3:
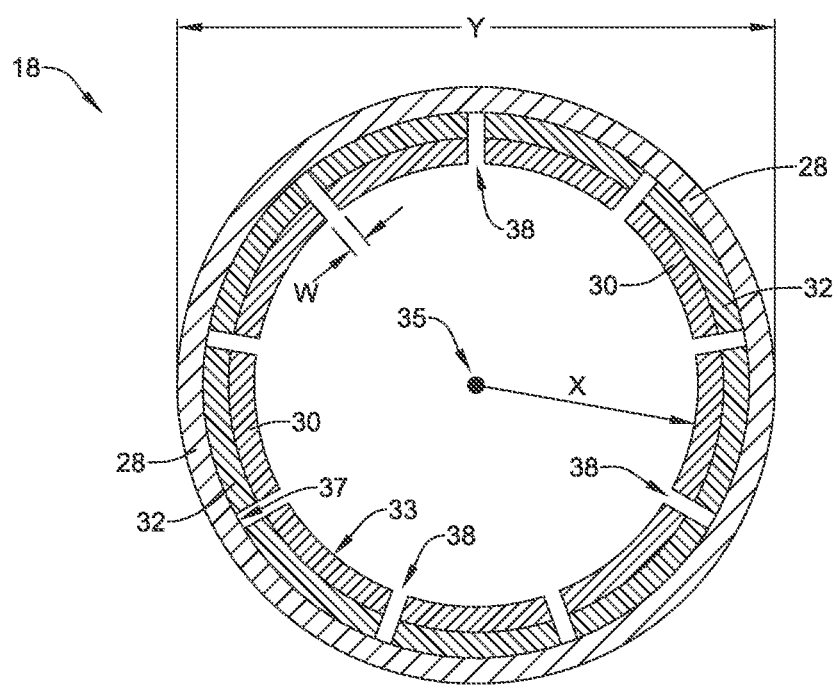
FIG. 3 is a cross-sectional view of an example introducer taken along the line 3-3 of FIG. 1.

FIG. 3 shows a cross-sectional view along line 3-3 of FIG. 1. FIG. 3 illustrates a cross-section taken along the distal section 18 of the tubular member 14. As will be described in greater detail below, FIG. 3 represents a cross-section of the distal section 18 of the tubular member 14 in an unexpanded configuration.

FIG. 3 further illustrates that the distal section 18 of the tubular member 14 may include an inner layer 30, a reinforcement layer 32 and an outer layer (e.g., sheath, jacket, covering, etc.) 28. The inner layer 30 may include an inner surface 33.

As shown in FIG. 3, the distal section 18 of the tubular member 14 may include an outer diameter depicted as "Y." Further, the distal section 18 of the tubular member 14 may include an inner radial extent (measured from the longitudinal axis 35 of the distal section 18 to the inner surface 33 of the distal section 18) depicted as "X."

As shown in FIG. 3, the distal section 18 may include a reinforcement layer 32 positioned between the inner layer 30 and the outer layer 28. The reinforcement layer 32 may be designed to provide increased stiffness and/or increased axial strength to the distal section 18. In other words, the reinforcement layer 32 may provide increased resistance to buckling of the distal section 18. Additionally, FIG. 3 illustrates that, in some examples, the reinforcement layer 32 may extend circumferentially around the longitudinal axis 35 of the introducer 10. Further, reinforcement layer 32 may include one or more reinforcement spines, ribs, etc.

As discussed above with respect to FIG. 1, FIG. 3 further illustrates that the distal section 18 of the introducer 10 may include one or more channels 38 extending radially outward from the inner surface 33 of distal section 18 of the tubular member 14. For example, FIG. 3 shows nine channels 38 positioned circumferentially around the longitudinal axis 35 of the distal section 18 of the tubular member 14. However, while FIG. 3 shows nine channels 38 positioned around the longitudinal axis 35 of the distal section 18 of the tubular member 14, it is contemplated that more greater or less than nine channels may be utilized for any example introducers 10 contemplated herein. For example, tubular member 14 may include 1, 2, 3, 4, 5, 6, 7, 8, 9, 10, 15 or more channels 38 positioned within tubular member 14.

Further, FIG. 3 depicts the width of the example channels 38 as "W." In some examples, width "W" may be about 0.025 mm to 1.0 mm, or about 0.100 mm to 0.750 mm, or about 0.150 mm to 0.500 mm, or about 0.250 mm.

Figure 6:
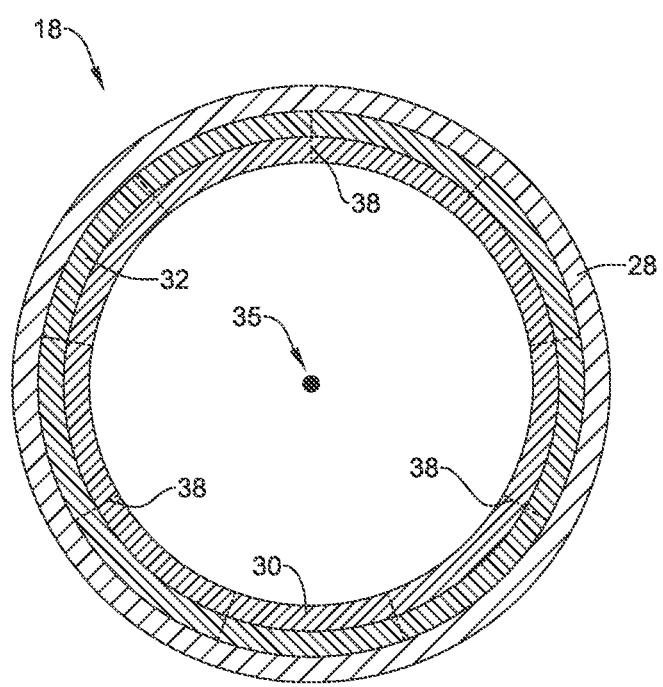
FIG. 6 is a cross-sectional view of another example introducer in an unexpanded configuration.

However, as described above, in some examples the channels 38 may be defined as merely preferential tear lines and or longitudinally extending perforations (as will be illustrated and discussed further with respect to FIG. 6 below). In other words, in some examples the channels 38 illustrated in FIG. 3 may not appear to have a defined width "W" (such as that illustrated in FIG. 3), but rather, may define a preferential tear line and/or perforation which is designed to separate as the distal section 18 expands radially outward.

As discussed above, FIG. 3 illustrates that channels 38 extend radially outward from the inner surface 33 of the inner layer 30. Further, FIG. 3 illustrates that, in some examples, the channels 38 may extend from the inner surface 33 of the inner layer 30 through the entire wall thickness of the inner layer 30 and, further, through the entire wall thickness of the reinforcement layer 32. In other words, in some examples, the channels 38 may extend from the inner surface 33 of the inner layer 30 to the inner surface 37 of the outer layer 28.

However, while FIG. 3 illustrates the channels 38 of distal section 18 extending from the inner surface 33 of the inner layer 30 to the inner surface 37 of the outer layer 28, it is contemplated that in at least some embodiments contemplated herein, the channels 38 may extend only partially into the reinforcement layer 32 or may extend only partially into the inner layer 30.

FIG. 3 further illustrates that each of the channels 38 may be circumferentially spaced apart from one another around the longitudinal axis 35 of the distal section 18 of the tubular member 14. In some instances, the channels 38 may be spaced substantially equidistant from one another around the longitudinal axis 35 of the distal section 18. In other words, the spacing between adjacent channels 38 may be substantially equivalent. However, it is further contemplated that one or more of the channels 38 may be spaced at variable distances around the longitudinal axis 35.

As discussed above, in some examples it may be desirable to design the introducer 10 to permit a medical device (e.g., heart valve) to pass therethrough. For example, it may be desirable to permit a medical device to pass through the hub 12, the proximal section 16 and the distal section 18 (for example, to pass through the introducer 10 while being inserted into a body lumen). Further, in some instances it may be desirable to design the introducer 10 to radially expand such that it can accommodate devices which have an outer diameter greater than the unexpanded inner diameters of the hub 12, the proximal section 16 and the distal section 18.

Figure 4:
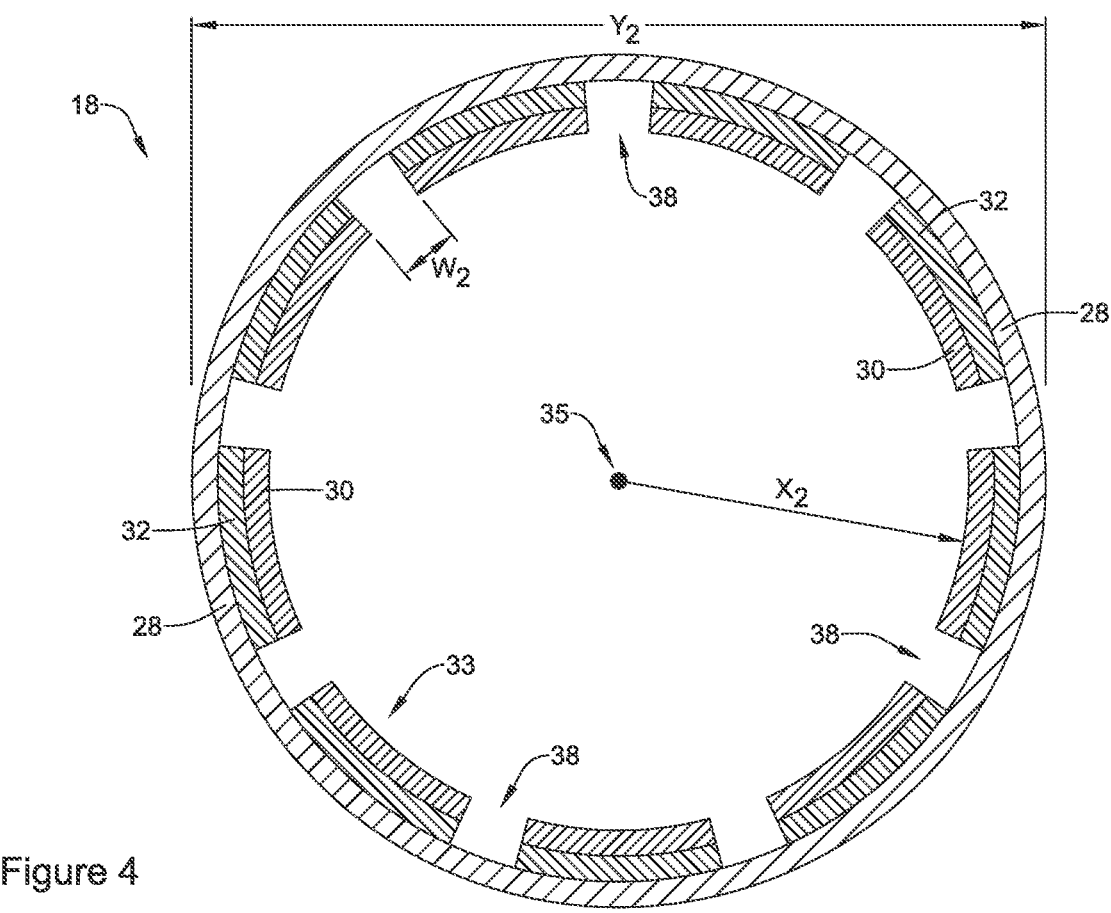
FIG. 4 is a cross-sectional view of the example introducer of FIG. 1 in an expanded configuration.

FIG. 4 represents the distal section 18 of the tubular member 14 in an expanded configuration. In other words, FIG. 4 may represent the cross-section of the tubular member 14 shown in FIG. 3 after it has been expanded radially outward.

As shown in FIG. 4, the distal section 18 of the tubular member 14 may include an outer diameter depicted as "$Y_2$." It can be appreciated that the expanded outer diameter $Y_2$ may be greater than the unexpanded diameter Y shown in FIG. 3. In some examples, diameter "$Y_2$" may be about 0.5% to 400% greater than diameter "Y," or about 1% to 300% greater than diameter "Y," or about 10% to 200% greater than diameter "Y," or about 50% to 150% greater than diameter "Y," or about 125% greater than diameter "Y." Further, the distal section 18 of the tubular member 14 may include an expanded inner radial extent (measured from the longitudinal axis 35 of the distal section 18 to the inner surface 33 of the distal section 18) depicted as "$X_2$." It can be appreciated that the expanded inner radius $X_2$ may be greater than the unexpanded inner radius X shown in FIG. 3.

It can be appreciated that as an example introducer 10 is expanded from an unexpanded configuration to an expanded configuration (as shown in FIG. 3 and FIG. 4), the total wall thickness of the distal section 18 (including the thickness of the outer layer 28, the reinforcement layer 32 and/or the inner layer 30) may decrease. In other words, as the distal section 18 of the tubular member 14 expands, the material defining the distal section 18 (including the outer layer 28, the reinforcement layer 32 and/or the inner layer 30) may stretch as the distal section 18 of the tubular member 14 expands radially outward. This stretching of the distal section 18 of the tubular member 14 may cause the wall thickness of the distal section 18 to decrease.

Additionally, it can be appreciated that as the distal section 18 of the tubular member 14 expands, the width of the channels 38 may increase. For example, FIG. 4 shows the width of the channels 38 in an expanded configuration as "$W_2$." In other words, the width $W_2$ may be greater than W (depicted in FIG. 3). Further, it can be appreciated that the distal section 18 of the introducer 10 may be designed such that as the distal section 18 expands from an unexpanded configuration to an expanded configuration, the inner layer 30 and the reinforcement layer 32 may separate and widen (or "split" and widen for examples in which the channels 38 define perforation lines) along the channels 38. Further, as the distal section radially expands, it is contemplated that the outer layer 28 may remain continuous around the inner layer 30 and the reinforcement layer 32. In other words, as the channels 38 widen (as the distal section 18 expands) the outer layer may merely stretch without breaking, separating, splitting, etc. thereby maintaining a continuous outer surface around the inner layer 30 and the reinforcement layer 32.

Figure 5:
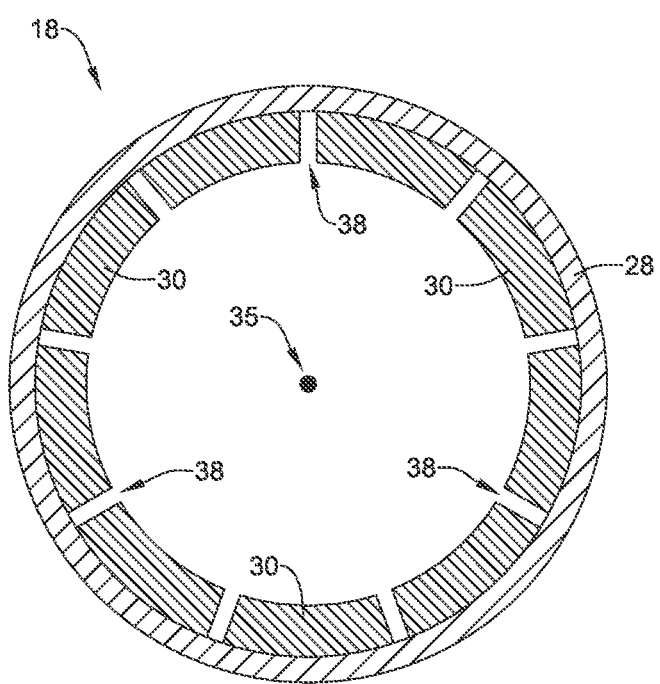
FIG. 5 is a cross-sectional view of another example introducer in an unexpanded configuration.

FIG. 5 illustrates a cross-section of another example distal section 18 of the tubular member 14. The example distal section 18 may be similar in form and function to other examples disclosed herein (such as the introducer 10 illustrated in FIG. 3). However, FIG. 5 further illustrates that the distal section 18 may include a single inner layer 30. For example, FIG. 5 illustrates an example distal section 18 which does not include a separate reinforcement layer positioned between the inner layer 30 and the outer layer 28. Rather, FIG. 5 illustrates distal section 18 which includes a single inner layer 30. However, as shown in FIG. 5, it can be appreciated that the wall thickness of the single inner layer 30 may be substantially equivalent to the combined wall thickness of the inner later 30 and the reinforcement layer 32 shown in FIG. 3. Further, it can be appreciated that in some examples, the inner layer 30 of FIG. 5 may be constructed from a material that allows the single inner layer 30 to maintain an axial strength which is similar to the axial strength of the reinforcement layer 32 combined with the inner layer 30 shown (and described above) with respect to FIG. 3.

As described above, in some examples the channels 38 described herein may be defined as a seam, preferential tear lines, longitudinally extending perforations, etc. For example, FIG. 6 shows an example cross-section of the distal section 18 (which may be similar in form and function to the cross-section shown in FIG. 3 and FIG. 5) which illustrates seam, preferential tear lines and/or perforations 38 positioned within the inner layer 30 and the reinforcement layer 32. FIG. 6 illustrates that the preferential tear lines or perforations 38 shown in FIG. 6 may not appear to have a defined width "W" (such as that illustrated in FIG. 3), but rather, may define a preferential tear line and/or perforation 38 which is designed to separate as the distal section 18 expands radially outward. It is contemplated that the unexpanded distal section 18 shown in FIG. 6, may expand separate along the preferential tear lines and/or perforations 38 to form an expanded configuration similar to that shown in FIG. 4.

Further, it is contemplated that the inner surface and/or outer surface of any of the examples described herein may include one or more layers or coatings, such as a lubricious coating, a hydrophilic coating, a hydrophobic coating, or other suitable coatings, and the like, or may include a lubricant disposed thereon.

In some examples, the example expandable introducer 10 may be disposed about or inserted over a guidewire (not shown), although the guidewire is not required. As discussed above, in some examples the expandable introducer 10 may include a proximal section 16 and a distal section 18. In examples having a proximal section 16, the proximal section 16 may have an inner diameter or extent sufficient to accept a medical device passing therethrough, while the distal expandable section 18 may have an inner diameter or radial extent in a relaxed condition that is less than a maximum outer diameter or extent of the medical device. The expandable introducer 10 may be formed using any of the techniques or structures discussed herein.

Figure 7:
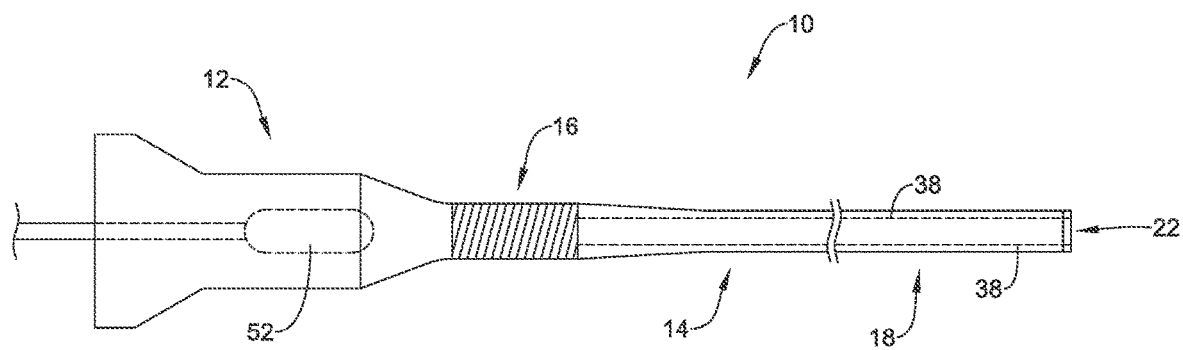
FIGS. 7-9 illustrate an example medical device being inserted through an example introducer.
Figure 8:
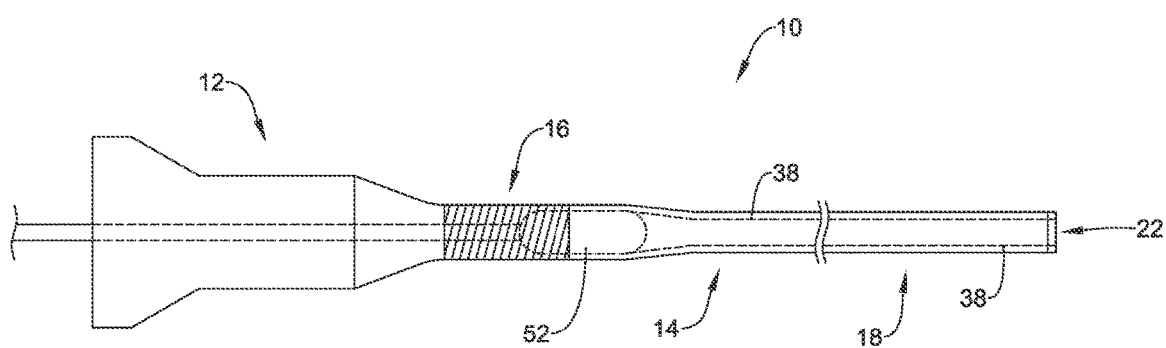
Figure 9:
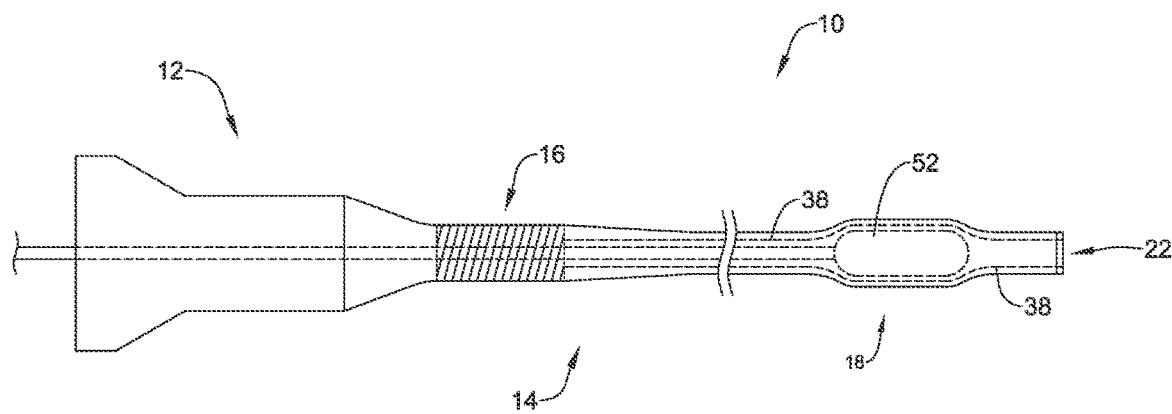

FIGS. 7-9 illustrate a method of use of introducer 10. FIG. 7 shows that an elongate medical device 52 (e.g., heart valve) may be inserted into the lumen 22 of the introducer 10 and advanced distally toward the distal end of introducer 10. As the medical device 52 reaches, encounters, and/or engages the lumen 22 of the introducer 10, the medical device 52 may exert a radially outward force from within the lumen 22 upon the wall of the tubular member 14 (e.g., on the inner surface 33 of the inner layer 30). The radially outward force may cause the tubular member 14 to expand radially outward as the medical device 52 is advanced distally through the proximal section 16 and/or the distal section 18.

FIG. 8 illustrates the medical device 52 being inserted through proximal section 16 and into the distal section 18. As can be appreciated from FIG. 8 and the above discussion, the distal section 18 may expand radially outward as the medical device 52 is inserted therethrough.

FIG. 9 illustrates the medical device 52 being positioned within the distal section 18 of the introducer 10. As can be appreciated from FIG. 9, the distal section 18 may expand radially outward in order to permit the medical device 52 to travel therethrough. Further, FIG. 9 illustrates the distal section 18 contracting (e.g., returning) to an unexpanded diameter as the medical device 52 travels therethrough. In other words, in some examples, the distal section 18 of the introducer 10 may be designed such that it can expand radially outward and then contract radially inward as the medical device 52 inserted therethrough. The expansion of the distal section 18 from an unexpanded configuration to an expanded configuration illustrated in FIG. 9 may correspond to the expansion from an unexpanded to an expanded configuration of the tubular members illustrated and described above with respect to FIGS. 3-6.

In some examples, introducer 10 may be made from materials such as metals, metal alloys, polymers, ceramics, metal-polymer composites, or other suitable materials, and the like. Some examples of suitable materials may include metallic materials such as stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymeric material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some examples, the introducer 10 may be made from materials such as, for example, a polymeric material, a ceramic, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. In some examples, a suitable polymeric material may have a yield strain of at least 20%, at least 30%, at least 40%, at least 50%, or more. In some examples, the sheath, the membrane, and/or the plurality of corrugations may be made from a material having a low coefficient of friction. In some examples, the sheath, the membrane, and/or the plurality of corrugations may be formed from a fluoropolymer, such as polytetrafluoroethylene (PTFE) or fluorinated ethylene propylene (FEP).

Portions of introducer 10 may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the elements described above (i.e., the sheath, the membrane, the medical device, etc.) may include or be formed from a radiopaque material. Suitable materials can include, but are not limited to, bismuth subcarbonate, iodine, gold, platinum, palladium, tantalum, tungsten or tungsten alloy, and the like.

It should be understood that although the above discussion was focused on percutaneous medical procedures within the vasculature of a patient, other examples or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures as appropriate. For example, in some examples, the devices may be deployed in a non-percutaneous procedure. Devices and methods in accordance with the disclosure can also be adapted and configured for other uses within the anatomy.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. An introducer sheath, comprising: a tubular member including an inner layer and an outer layer, the inner layer having an inner surface, an outer surface and wall extending therebetween and wherein the outer layer is disposed along the outer surface of the inner layer;
    wherein the inner layer includes a plurality of longitudinal channels extending radially outward from the inner surface;
    wherein each channel of the plurality of channels has a circumferential width;
    wherein the tubular member is designed to shift from an unexpanded configuration to an expanded configuration, and wherein the circumferential width of each channel increases as the tubular member shifts from the unexpanded configuration to the expanded configuration;
    wherein the tubular member includes an annular distal tip member;
    wherein the plurality of channels terminates at a proximal end of the annular distal tip member;
    wherein the tubular member includes a proximal section and a distal section, wherein the proximal section includes a spring member disposed therein;
    wherein the plurality of channels extends distally from an annular collar disposed proximate a distal end of the spring member.

2. The introducer of claim 1, wherein the outer layer extends continuously around the circumference of the inner layer in both the unexpanded configuration and the expanded configuration.

3. The introducer sheath of claim 1, wherein each channel of the plurality of channels extends from the inner surface through the wall of the inner layer.

4. The introducer sheath of claim 1, wherein the tubular member includes a first outer diameter in the unexpanded configuration and a second outer diameter in the expanded configuration, and wherein the second diameter is at least 125% of the first diameter.

5. The introducer sheath of claim 1, wherein the outer layer is free of the plurality of channels.

6. The introducer sheath of claim 1, wherein the plurality of channels includes 7-11 channels.

7. The introducer sheath of claim 1, wherein the introducer sheath includes a hub member attached to the tubular member, the tubular member including a proximal section and a distal section, and wherein the plurality of channels are distal of the proximal section.

8. The introducer sheath of claim 1, wherein the tubular member further comprises a reinforcement layer disposed between the inner layer and the outer layer.

9. The introducer sheath of claim 8, wherein the plurality of channels extend radially outward into at least a portion of the reinforcement layer.

10. An introducer sheath, comprising:
a shaft having an expandable portion and a tip member defining a distal end of the shaft and extending a full circumference of the shaft, the expandable portion positioned proximal to the tip member; and
an outer jacket disposed along an outer surface of the shaft;
wherein the expandable portion includes a plurality of longitudinal channels extending radially outward from an inner surface of the expandable portion;
wherein each channel of the plurality of channels has a circumferential width;
wherein both the expandable portion and the tip member are designed to shift from an unexpanded configuration to an expanded configuration, and wherein the circumferential width of each channel increases as the expandable portion shifts from the unexpanded configuration to the expanded configuration;
wherein the plurality of longitudinal channels terminates proximal of the distal end of the shaft;
wherein the tubular member includes a proximal section and a distal section;
wherein the proximal section includes a spring member disposed therein;
wherein an annular collar is directly coupled to the spring member;
wherein the distal section is attached to the annular collar;
wherein the plurality of channels extends distally from the annular collar.

11. The introducer of claim 10, wherein the tip member is free of the longitudinal channels.

12. The introducer sheath of claim 10, wherein the shaft includes a first outer diameter in the unexpanded configuration and a second outer diameter in the expanded configuration, and wherein the second diameter is at least 125% of the first diameter.

13. The introducer of claim 10, wherein the expandable portion includes an outer diameter in the unexpanded configuration, and wherein the tip member includes an outer diameter in the unexpanded state, and wherein the outer diameter of the expandable portion in the unexpanded state matches the outer diameter of the tip member in the unexpanded state.

14. The introducer sheath of claim 10, wherein the jacket is free of the plurality of channels.

15. The introducer sheath of claim 10, wherein the expandable portion further comprises an inner layer and a reinforcement layer, and wherein the reinforcement layer is disposed between the inner layer and the jacket.

16. The introducer sheath of claim 15, wherein the plurality of channels extend radially outward into at least a portion of the reinforcement layer.

17. The introducer sheath of claim 15, wherein the plurality of channels extend radially outward through both the inner layer and the reinforcement layer.

* * * * *